United States Patent
Tang et al.

(10) Patent No.: US 7,532,323 B2
(45) Date of Patent: May 12, 2009

(54) SPATIAL LIGHT MODULATOR APPARATUS AND METHOD

(76) Inventors: Cha-Min Tang, 6 Radnor Way, Radnor, PA (US) 19087-5134; Andrew Bartfay-Szabo, 425 Grand Pond Rd., North Andover, MA (US) 01845

(*) Notice: Subject to any disclaimer, the term of this patent is extended or adjusted under 35 U.S.C. 154(b) by 224 days.

(21) Appl. No.: 10/577,597

(22) PCT Filed: Oct. 28, 2004

(86) PCT No.: PCT/US2004/035637

§ 371 (c)(1),
(2), (4) Date: Apr. 27, 2006

(87) PCT Pub. No.: WO2005/043197

PCT Pub. Date: May 12, 2005

(65) Prior Publication Data

US 2007/0132998 A1    Jun. 14, 2007

Related U.S. Application Data

(60) Provisional application No. 60/514,888, filed on Oct. 28, 2003.

(51) Int. Cl.
*G01J 3/30* (2006.01)

(52) U.S. Cl. .................................................. 356/317
(58) Field of Classification Search .................. 356/317
See application file for complete search history.

(56) References Cited

U.S. PATENT DOCUMENTS

| | | | |
|---|---|---|---|
| 6,483,641 B1 | 11/2002 | MacAulay | |
| 6,794,658 B2 | 9/2004 | MacAulay | |
| 2001/0041843 A1* | 11/2001 | Modell et al. | ............ 356/317 |

OTHER PUBLICATIONS

Larry J. Hornbeck: Digital Light Processing for High-Brightness, High-Resolution Applications; (1997).

* cited by examiner

*Primary Examiner*—Kara E Geisel
(74) *Attorney, Agent, or Firm*—Edwards Angell Palmer & Dodge LLP; George N. Chaelas

(57) ABSTRACT

A device for discriminately illuminating a sample (22) to be viewed with excitation light (70). For example, an image taken with a CCD (10) provides feedback which is used to modulate the output of an excitation light source (40), thereby allowing a sample (22) to be viewed within the optimal range of detection for the particular CCD device (10) being used, despite the potential of wide dynamic ranges of sample luminescence.

18 Claims, 18 Drawing Sheets

PRIOR ART

Figure 4A
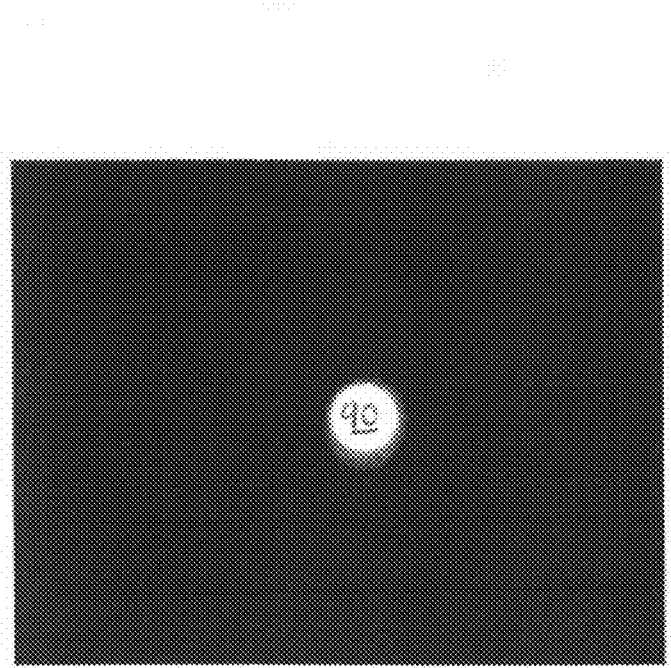
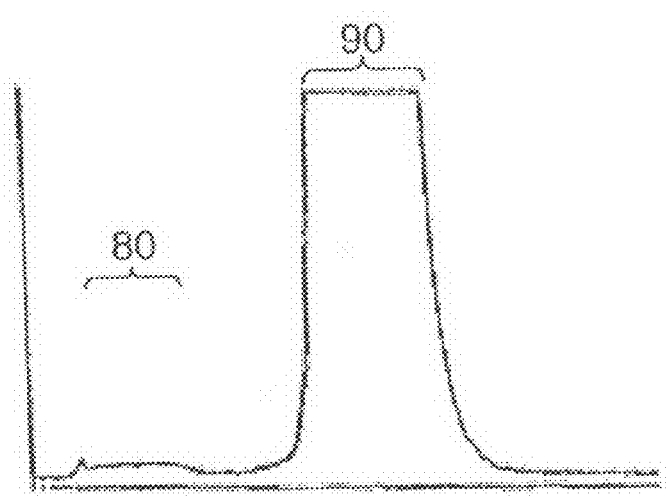
Figure 4D

Figure 4B
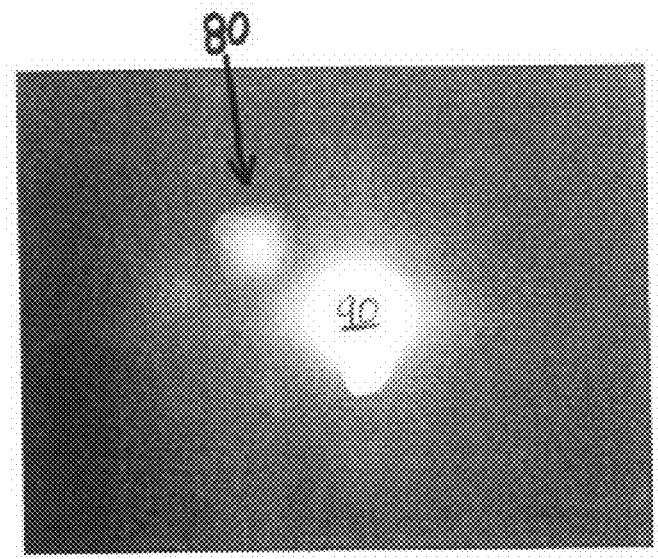
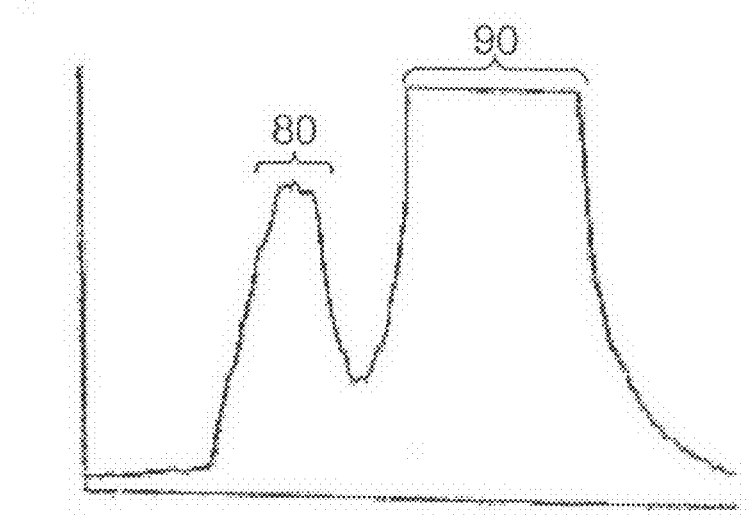
Figure 4E

Figure 4C
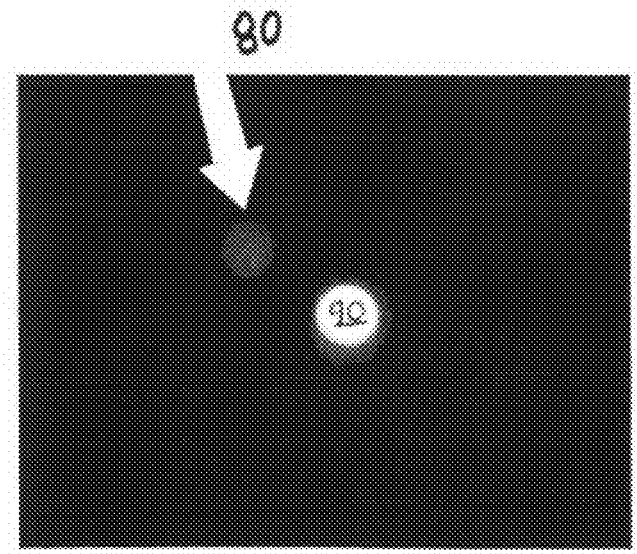
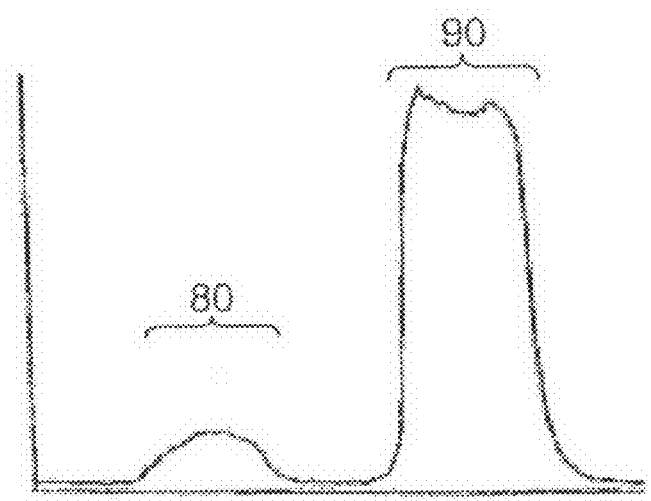
Figure 4F

Figure 10A  Figure 10B  Figure 10C  Figure 10D
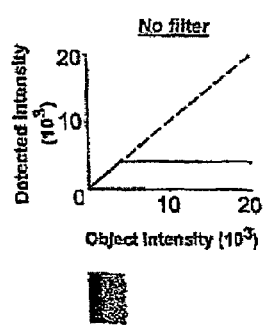
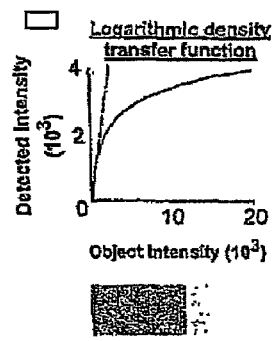
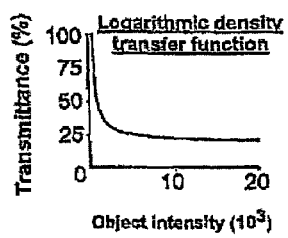
Figure 11A  Figure 11B  Figure 11C

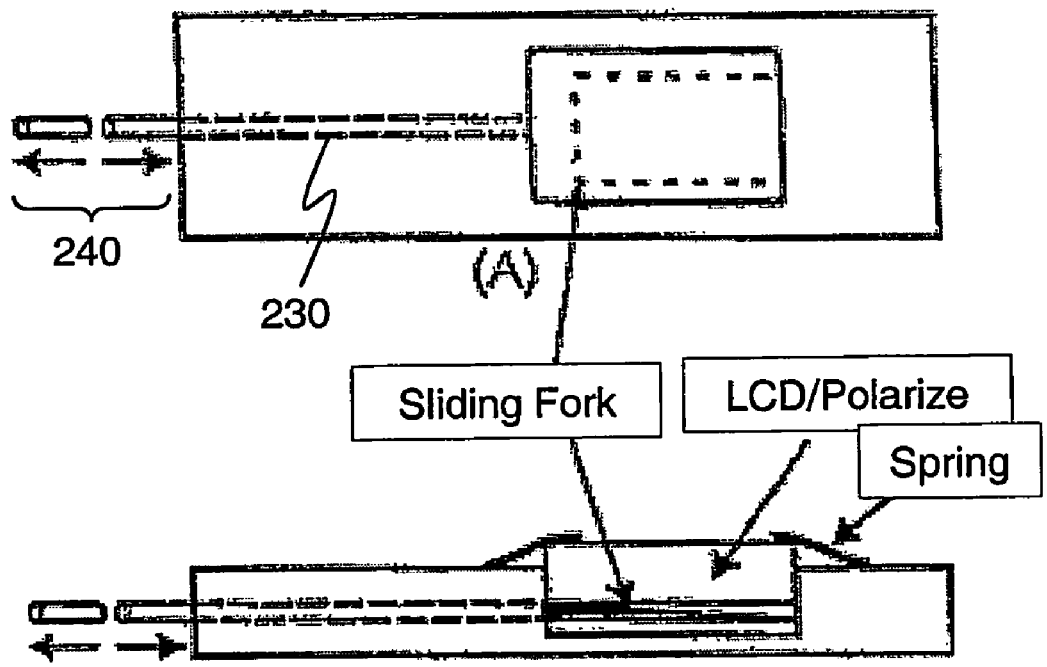

SPATIAL LIGHT MODULATOR APPARATUS AND METHOD

CROSS-REFERENCE TO RELATED APPLICATIONS

This application is the U.S. national phase, pursuant to 35 U.S.C. §371, of international application No. PCT/US2004/035637, published in English on May 12, 2005 as international publication No. WO 2005/043197 A2, which claims the benefit of Provisional Application No. 60/514,888, filed Oct. 28, 2003, the disclosure of which applications are incorporated herein in their entireties by this reference.

FIELD OF THE INVENTION

This invention relates to microscope systems that utilize spatial light modulators for illuminating a specimen, for example, fluorescent microscopes.

BACKGROUND OF THE INVENTION

Microscopes are well-established instruments for observing minute biological structures and processes. This field of art includes fluorescent microscopy, which allows a user to achieve a high degree of target specificity and image contrast for biological specimens. Conventional fluorescent microscopes employ the basic illumination scheme shown in FIG. 1. In FIG. 1, a viewing device 10 (such as a Charged Coupled Device (CCD) or camera or eye) is used to observe a biological sample 22 which rests upon stage 20. The viewing device 10 includes a viewing path through an image forming tube lens 26, an emission filter 34, a dichroic mirror 30, and an objective lens 24.

A lamp 40 emits an excitation light 50 that has passed through the collector 32 and which then passes through the conjugate image plane located at the field diaphragm 42. The excitation light 50 continues through the projection tube lens 28 and an excitation filter 36. The excitation light 50 is of a wavelength that is reflected downward by the dichroic mirror 30, after which it passes through objective 24 to thereby reach sample 22 where the excitation light 50 stimulates a fluorescent marker in the sample 22. The sample 22, thus excited, emits a fluorescent emission which is of a wavelength permitted to pass through the dichroic mirror 30, and which is viewed by the viewing device 10.

Known methods for illuminating a biological specimen in fluorescent microscopy utilize an even excitation illumination across the entire field of view. For instance, Kohler illumination applies an even excitation light across an entire sample. Problems arise from these known systems of illumination, however, as there are situations where it may be better to vary the intensity of illumination over different regions of the specimen.

For instance, during live cell imaging only a portion of the field of view is of interest and unnecessary exposure of light to living tissue in the remainder of the field can result in photo-toxicity and/or photo-bleaching. An additional problem occurs when a bright object is located in front or in back of a structure of interest, making it impossible to clearly view the object of interest.

Photo-toxicity is a particularly troubling problem in live cell fluorescence microscopy. First, fluorescence microscopy requires very intense excitation illumination that is typically many orders of magnitude brighter than that used for conventional brightfield microscopy. Photo-toxicity due to an intense excitation illumination light is often the ultimate limitation in live cell fluorescence imaging. Secondly, all fluorescent dyes produce toxic free radicals upon illumination with excitation light.

The current invention minimizes photo-toxicity and photo-bleaching through control of the excitation illumination, for instance, by modulating the intensity of the excitation light through at least one of spatial modulation and temporal modulation. In spatial modulation, different regions of the specimen are simultaneously illuminated with different intensities of excitation light based on the needs and interests of the observer. In temporal modulation, different regions of the specimen are scanned by an excitation light of varying intensity over a time period.

Electronic image sensors and detectors have replaced photographic cameras as the primary means to record images in wide-field fluorescence microscopy. An inherent weakness of current digital detectors is a limited ability to record images with high variations in brightness. This becomes a serious problem when sub-regions of a sample are much brighter than the regions of interest. The bright regions saturate the detector while the regions of interest are inadequately illuminated. These problems are discussed below in relation to FIGS. 2A-2C.

Image quality depends upon the proper biasing of illumination brightness so as to stay within the optimal detection range of the CCD detector. Under-excitation results in a poor signal-to-noise ratio. An example of under-excitation is shown in FIG. 2A, where the image of the sample was acquired under insufficient illumination. Other problems result from over-excitation. As shown in FIG. 2C, the sample being viewed was over-excited, resulting in pixel saturation at the CCD. Note that the image is distorted, leaving no plausible manner in which to perform quantitative analysis.

As shown in FIG. 2B and so long as the sample being viewed has relatively low variations in brightness between various portions of the sample, it should be possible to find a proper level of excitation illumination that can produce a qualitatively pleasing and quantitatively accurate image. However, with current microscopes, and when a sample's emitted brightness possesses moderate-to-high variability, it has been heretofore impossible to select a single proper level of excitation illumination (i.e., exposure duration) that will produce optimized imaging for each aspect of a sample being viewed.

SUMMARY OF THE INVENTION

The present invention provides an apparatus and method for minimizing photo-toxicity during live cell imaging. Secondly, the present invention enables fluorescent samples with widely varying brightness to be optimally recorded with electronic detectors by spatially modulating the intensity of illumination. The degree of modulation at each spatial location is recorded and can be subsequently used to reconstruct a quantitatively accurate image that is not distorted by the limitations of the electronic detector. Thirdly, the present invention further relates to a confocal mask using spatial light modulation and including computer readable means to implement the above. Details of the present invention are further described in the Detailed Description of Embodiments section, below.

BRIEF DESCRIPTION OF THE DRAWINGS

The invention, both as to its organization and manner of operation, may be further understood by reference to the drawings that include FIGS. 1-18C, taken in connection with the following detailed description of exemplary embodiments.

FIG. 4A is an image taken of two spheres of differing brightness, wherein the first, dimmer sphere cannot be clearly detected above background noise while the brighter, second sphere has reached saturation;

FIG. 4B is an image taken of the same two spheres of FIG. 4A, except illumination has been increased until the dim sphere can be clearly observed, resulting in the bright sphere surpassed detector saturation;

FIG. 4C is an image of the same two spheres using the discriminate stimulating light modulation of the present invention, thereby allowing both spheres to be clearly detected and amenable for quantitatively analysis;

FIG. 4D is a graphical representation of the luminescence produced by the two spheres in FIG. 4A;

FIG. 4E is a graphical representation of the luminescence produced by the two spheres in FIG. 4B;

FIG. 4F is a graphical representation of the luminescence produced by the two spheres in FIG. 4C;

FIGS. 10A-D illustrate examples of constructed field iris masks according to an embodiment of the invention;

FIG. 11A illustrates a linear graph of intensity of detected luminance at an image detector as compared to the luminance intensity of a sample being viewed without any type of masking;

FIG. 11B illustrates a graph of intensity of detected luminance at an image detector as compared to the luminance intensity of a sample being viewed using a logarithmic density transfer function as an automated mask;

FIG. 11C illustrates a graph of intensity of detected luminance at an image detector as compared to the luminance transmittance of a sample being viewed using a logarithmic density transfer function as an automated mask;

FIG. 14A illustrates a top view of an embodiment of the invention including a sliding fork that is capable of moving an LCD to thereby adjust the focus of a projected image;

FIG. 14B illustrates a side view of the sliding fork shown in FIG. 14A, wherein the sliding fork allows a projected image to be adjusted for focus;

DETAILED DESCRIPTION OF EMBODIMENTS

Enabling examples of the present invention provided herein discuss an epi-illumination fluorescent microscopy apparatus. However, the ordinarily skilled artisan readily comprehends that the invention may be deployed in any type of illumination system utilizing fluorescent microscopy, and/or in non-microscopy applications involving fluorescent emissions. Those of skill in the art readily comprehend that the instant invention may be deployed with any type of stimulating light illumination system used for stimulating a sample to produce excited fluorescence and/or for confocal masking.

Achieving optimal image quality using a CCD detector requires that the sample being viewed possess an emitted light signal intensity that is within the linear range of the CCD. The present invention achieves this goal by adaptively modulating excitation illumination intensity on a pixel-by-pixel basis using a high resolution spatial light modulator, such as an LCD (liquid crystal display) or a DMD (digital micro-mirror device). The degree of modulation may be saved and later retrieved, thereby allowing reconstruction of a quality image with a high degree of accuracy and with highly favorable signal-to-noise characteristics. The dynamic range of the signal to be recorded may first be compressed to remain within the distortion free range of the recording device. If desired, the dynamic range of the recorded signal can then be uncompressed for quantitatively accurate and distortion free playback.

The phrase "pixel-by-pixel," as used herein, describes the ability of the instant invention to modulate excitation illumination on a point-by-point and/or an area-by-area basis, and may therefore include any range of a number of pixels, from the lowest degree of resolution to the highest. Further, the present invention does not require that a certain number of pixels at an illumination device correspond directly to the same number (or any certain number) of pixels at an imaging device.

Figure 1:
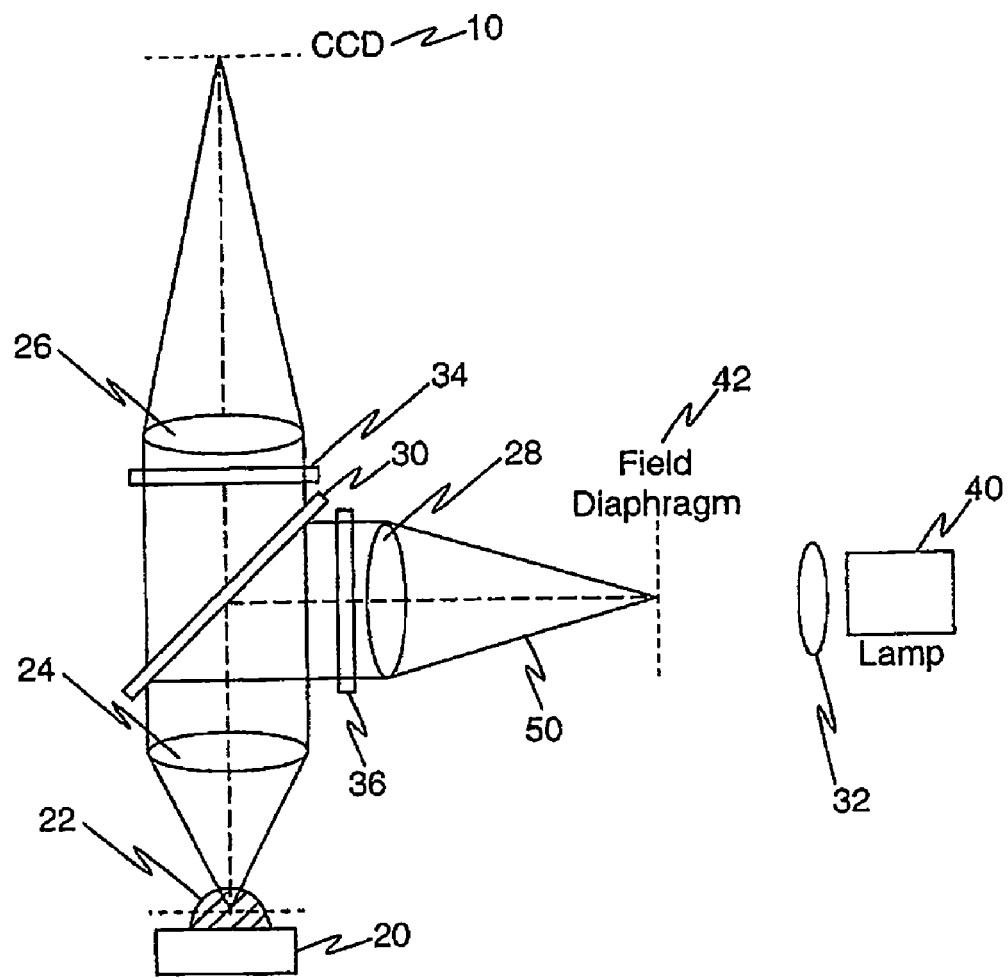
FIG. 1. is an illustration of a prior art excitation light illumination system capable of being used with a fluorescent microscope.
Figure 2C:
FIG. 2C is the same dendrite of FIGS. 2A and 2B, but taken with excessive excitation illumination.
Figure 2B:
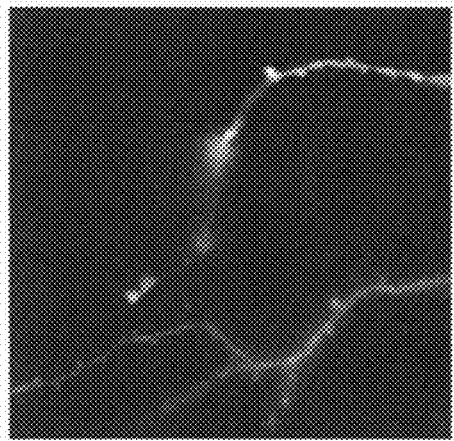
FIG. 2B is the same dendrite of FIG. 2A, but which has received sufficient excitation illumination.
Figure 2A:
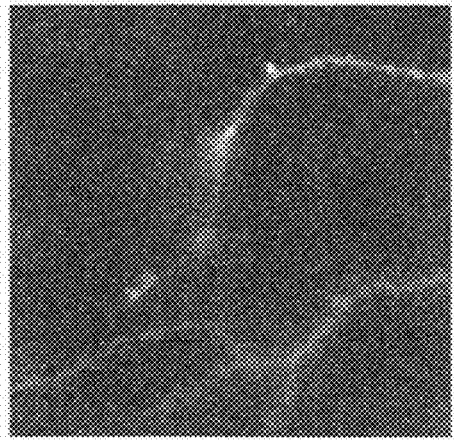
FIG. 2A is an image of a dendrite of a live green fluorescent protein (GFP) labeled neuron that has not received sufficient excitation illumination.
Figure 3:
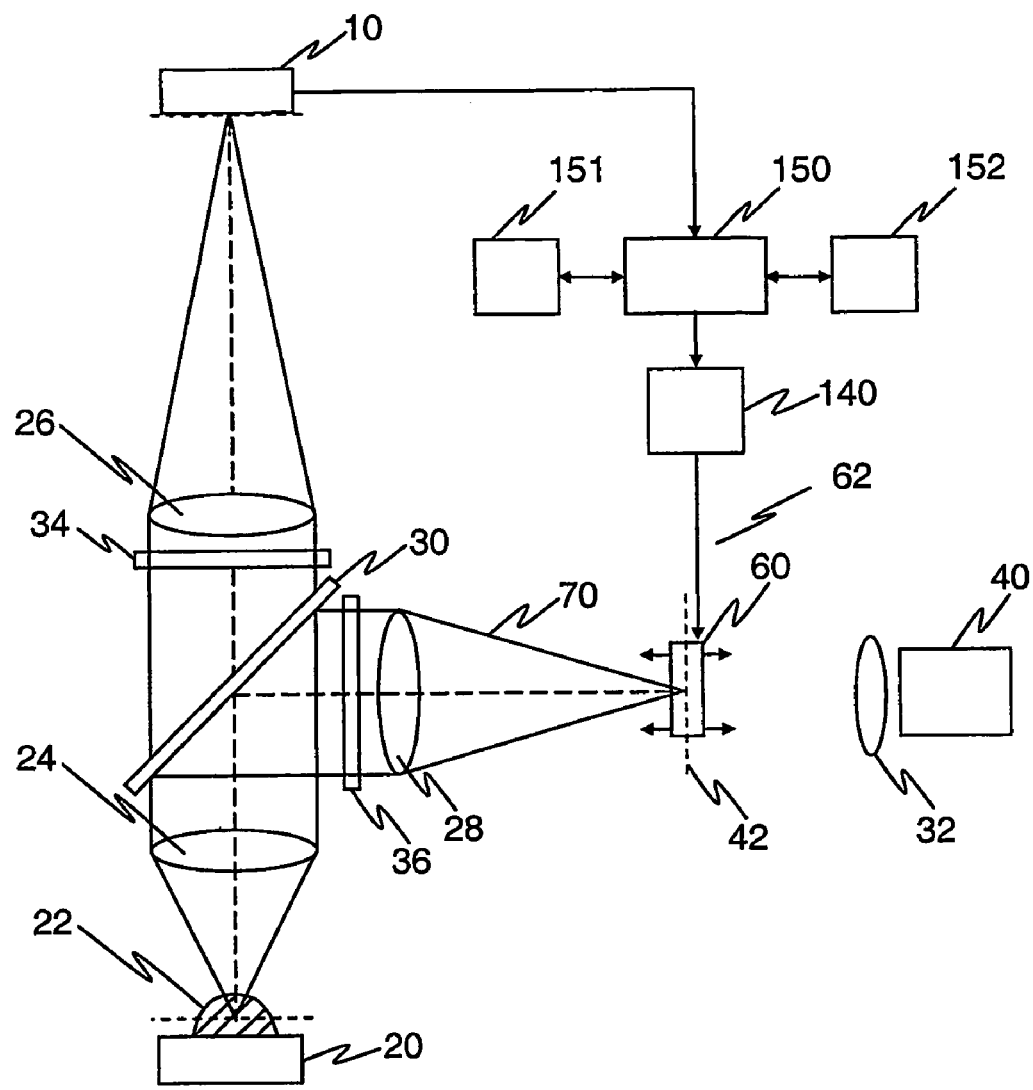
FIG. 3 is an embodiment of the present invention including a spatial light modulator enabling discriminate excitation illumination modulation on a region-by-region basis of the sample under observation.

FIG. 3 illustrates an embodiment of the present invention as implemented in a fluorescent imaging system. Similar features previously discussed in relation to FIG. 1 are not re-discussed so as to avoid redundancy.

As shown in FIG. 3, an imaging device 10 is used to observe a biological sample 22 through the dichroic mirror 30. The imaging device 10 may be a charged coupled device (CCD), an intensified camera, a complementary metal oxide semiconductor (CMOS) camera, a video camera, a photodiode detector array, or another imaging device. A light source 40 produces a light that is transmitted to a spatial light modulator 60. Spatial light modulator 60 receives feedback from the CCD 10 via feedback loop 62. The feedback provided by feedback loop 62 allows for modulation of the excitation light at the modulator 60. Modulation of the excitation light is achieved using computer 150, and includes modulating in at least a grayscale manner and based on information provided from at least the CCD 10.

The phrase "grayscale manner" is used to describe the ability of the instant invention to control the precise excitation illumination intensity of each individual pixel in the modulator, thereby providing gradients of light intensity at each individual pixel ranging from zero intensity to the highest intensity that the modulator 60 is capable of. An embodiment of the present invention modulates at least one of the spatial location of the illuminated pixels and the gray levels of the modulator's (element 60) pixels to discriminately excite the sample being viewed (such as sample 22 shown in FIG. 3). In an additional embodiment, both spatial and grayscale modulation may be used. In yet a further embodiment, an all-or-none (binary) modulation may be used.

While the high resolution spatial light modulator 60 may comprise an LCD, a digital micro-mirror device, or another light modulating device, the embodiment shown in FIG. 3 uses an LCD. In this embodiment, an input polarizer positioned on the same side of the LCD panel as the light source provides the LCD panel with a uniform, linearly polarized cone of light. Each pixel in the LCD panel can thus independently rotate the input polarized light to an angle dictated by a voltage addressed to that pixel. The exit polarizer positioned towards the specimen then absorbs the rotated light to an extent dictated by the degree of rotation to create an image of differing intensities. The input polarizer, the LCD of the transmissive type, and the exit polarizer are illustrated as a single device in this application.

Spatial light modulator 60 can thereby transmit a modulated excitation light 70 which is of the wavelength reflected by the dichroic mirror 30 onto the sample 22, where a fluorescent marker in the sample 22 is stimulated. The sample 22, thus excited, emits a fluorescent emission which is of a wavelength permitted to pass through the dichroic mirror 30, and which is recorded by the imaging device 10.

In contrast to the device of FIG. 1, the sample 22 of FIG. 3 may be adaptively and discriminately illuminated with varying amounts of modulated excitation light 70 on either of, or any combination of, a spatial, a binary, and grayscale basis, thereby allowing a viewer to alter the ultimate amount of emission light produced in various portions of the sample. Modulation is based on feedback information provided by the feedback loop 62 and is controlled by computer 150. Alternatively, or in conjunction with the feedback, monitor 151 and graphical user interface 152 provide users with the ability to manipulate the computer 150 to thereby control the modulation of modulator 60 through the LCD controller 140.

The modulator 60 may be controlled by the computer 150 through the LCD controller 140 in a completely automated fashion wherein information received from the CCD 10 automatically drives the type of modulation instruction provided to modulator 60. For instance, if the sample 22 emits fluorescence near the upper limit of the CCD's effective range of detection, the computer 150 is capable of modulating the modulator 60 in a grayscale manner to lessen the intensity of the stimulating light reaching the portions of the sample 22 which are emitting near the upper limit of the CCD's effective range of detection, thereby lessening the intensity of the fluorescence emitted by the sample 22.

Further, the computer 150 provides the function of modulating the modulator 60 in a semi-automatic fashion. For instance, fluorescent emissions detected at the CCD 10 may be displayed on the display 151, along with potential patterns of suggested modulation based upon prior viewing of particular types of samples or based upon patterns of detected fluorescence as processed by an algorithm within computer 150. Additionally, the computer 150 provides the function of modulating the modulator 60 in a fixed pattern, regardless of the nature of the sample being viewed. For instance, the modulator 60 may be instructed to emit a rectangular field iris or a flexible field iris of any shape. Users are provided the option of manipulating any of the above examples in regards to space, shape, and intensity of the illuminating light through use of the computer 150 and the graphical user interface 152. The present invention's features of automated and semi-automated control of the excitation light modulator 60 are further discussed below in relation to FIGS. 11A-11C.

The degree of modulation implemented at each pixel of the spatial light modulator 60 is capable of being stored in a memory which can subsequently be retrieved to reconstruct a quantitatively accurate and distortion free image of the specimen. Reconstruction can be carried out by the computer through multiplication of the intensity recorded by the detector 10 with the feedback attenuation sent to the corresponding pixel on the spatial light modulator 60. Additionally and/or alternatively, reconstruction can be carried out by the computer through multiplication of the intensity recorded by the detector 10 with the feedback attenuation sent to the corresponding pixel, in conjunction with an optical transfer function (optical transfer functions are discussed herein in relation to FIGS. 11A-C) of the spatial light modulator and the illumination optical system. Further, reconstruction can also be carried out through use of a user input in conjunction with the previous.

FIGS. 4A-4F illustrate a comparison of the emission images resulting from prior art excitation illumination systems (e.g., the prior art illumination system of FIG. 1) in comparison with an embodiment of the present invention (e.g., the embodiment of the invention depicted in FIG. 3). FIGS. 4A-4F each include images captured from the same two spheres, 80 and 90 (sphere 80 fails to be depicted in FIG. 4A for reasons discussed below).

FIG. 4D is a graph corresponding to the emission brightness produced by the two spheres 80 and 90 as shown by the image detected by a CCD in FIG. 4A. Conventional widefield microscopy methods utilizing a scientific grade 12-bit CCD camera (Photometrics SenSys 1401™) can barely detect the faint sphere 80 at the same time that the bright sphere 90 has already saturated the pixels of the imaging device (as shown in FIG. 4A). This conventional method of producing an image relates to the prior art system depicted in FIG. 1, for instance. As shown in FIG. 4A, the sphere 80 is not yet properly excited so as to be properly imaged, while the sphere 90 has reached sufficient exposure of excitation light so as to reach saturation. These results are depicted in the graph of FIG. 4D, where sphere 80 possesses a negligible excited fluorescence emission in comparison to the excited fluorescence emission of the sphere 90.

FIG. 4E is a graph corresponding to the excitation illumination produced by the two spheres 80 and 90 as shown by the image detected by a CCD in FIG. 4B. This conventional method of producing an image relates to the prior art system depicted in FIG. 1, for instance. When the excitation exposure is increased to image the faint sphere 80, the image of the bright sphere 90 becomes grossly distorted (as shown in FIG. 4B). Notice that the bright sphere 90 appears falsely larger than its actual size. Sphere 80 and 90 are actually the same size, but exhibit differing brightness. Because the pixels surrounding the sphere 90 have become saturated, electron spillover has spread to neighboring pixels and post-acquisition image processing cannot be used to determine the true dimensions.

FIG. 4F is a graph corresponding to the emission illumination produced by the two spheres 80 and 90 as shown by the image detected by a CCD in FIG. 4C. Both the graph of FIG. 4F and the image of FIG. 4C have been created from an image and data resulting from the use of an embodiment of the present invention. In this embodiment, a high resolution spatial light modulator such as element 60 in FIG. 3 is used to provide adaptive and discriminate feedback-controlled excitation illumination.

For example and referring to FIG. 3 in addition to FIGS. 4C and 4F, an imaging device 10 takes an initial image of a sample 20 excited by modulated excitation light 70 from the high resolution spatial light modulator 60. If the resulting image is undesirable (e.g., if the image is similar to that shown in FIGS. 4A, 4B, 4D, and/or 4E), the excitation light may be modulated to produce a more qualitatively pleasing image. For example, in a non-limiting, enabling embodiment of present invention, the sample 20 is stimulated with excitation light 70, wherein the excitation light 70 is modulated to be an inverted illumination of the sample's previously detected fluorescent emissions.

"Inverted," as used herein, describes the application of a greater intensity of excitation light to those points in a sample that exhibit fluorescent emittance properties of lesser luminance and a lesser intensity of excitation light to those points in a sample that exhibit fluorescent emittance properties of greater luminance. Stated differently, bright pixels (as detected at CCD 10) are converted to dark pixels for purposes of modulating the excitation light 70. As used herein, "excitation" is generally used to describe the light deriving from the light source 40, and "emitted fluorescence" or "emission(s)" is generally used to describe the light fluorescing from the sample once excited. Other terms could be employed, however, to possibly include the use of "stimulated" instead of "excitation" and/or "excited" or "excited emission" instead of "emission" or "emitted fluorescence."

Using the initially detected fluorescent emission as feedback for an inverse level of excitation light provides the qualitatively pleasing image shown in FIGS. 4C and 4F, for example. The ordinarily skilled artisan readily comprehends that the excitation light does not need to be a linearly inverse of the detected fluorescent emission to derive the benefit of the invention, however. Indeed, the excitation light may be modulated to any lesser or greater degree to derive a qualitatively pleasing image, depending on the precise requirements of the sample being viewed through use of the invention's ability to cast light from the modulator 60 in a grayscale manner.

Figure 17A:
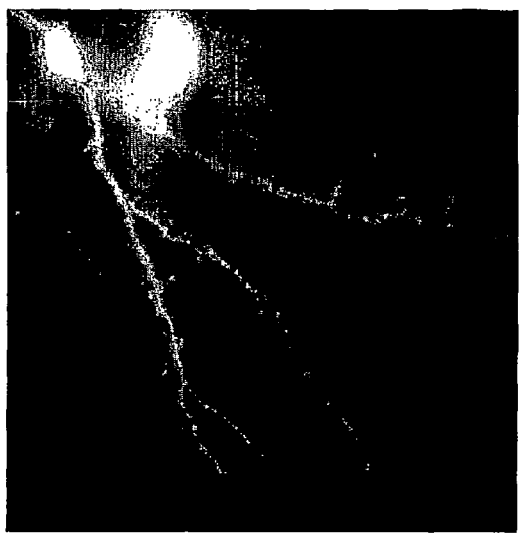
FIG. 17A is an image taken using a conventional homogenous epi-illumination system of a live neuron expressing green fluorescent protein (GFP)
Figure 18A:
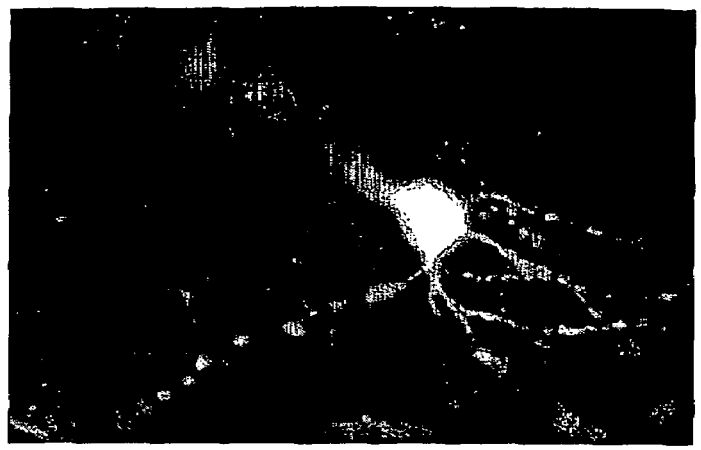
FIG. 18A is an image showing the pathological appearance of a fluorescently labeled neuron exhibiting photo-toxicity from excessive illumination.

FIGS. 17A and 18A are images taken of fluorescently labeled neurons using conventional excitation illumination methods. The image of FIG. 17A illustrates a live neuron expressing green fluorescent protein (GFP) taken using a conventional homogenous epi-illumination system. Note that the brightness of the cell body has saturated the image as detected by the imaging device, creating distortions to the size of the cell body that cannot be corrected, but that the distal dendritic branches are barely detectable. Furthermore, the glow from the bright cell body has created a false relative brightness of proximal dendrites compared to distal dendrites.

Figure 17B:
FIG. 17B is an image of the same neuron shown in FIG. 17A, but taken using the excitation light modulation apparatus of the present invention, thereby allowing for viewing of fine structures such as dendrite spines even out to the distal tips of the neuron.

In comparison, the image of FIG. 17B was taken of the same neuron but using the excitation illumination modulation of the instant invention. Note that the cell body is not saturated and therefore does not appeal to be (falsely) larger than it actually is. The fine structures of the dendrites such as the dendrite spines can be fully appreciated out to the most distal tips. Furthermore, the false brightness of the proximal dendritic processes shown in FIG. 17A has been eliminated.

FIG. 18A illustrates the typical pathological appearance of a fluorescently labeled neuron associated with photo-toxicity due to excessive exposure to excitation illumination using a convention illumination system. Note the formation of bead-like dilatations along axonal processes and the formation of blebs at dendritic branch points. Without masking of the bright cell body the previously noted pathological changes appear quite rapidly.

Figure 18B:
FIG. 18B is an image showing similar pathological appearance in another neuron; this neuron, however, was able to tolerate the same general level of illumination for a four-fold greater duration than that for the neuron shown in FIG. 18A; this increased tolerance was achieved through partial masking of the bright cell body using an embodiment of the present invention.

Contrastingly, FIG. 18B illustrates the appearance of another neuron wherein the cell body has been partially masked using the excitation modulator of the instant invention. This cell was able to tolerate a four-fold increase in exposure time at the same overall intensity to reach a comparable degree of injury.

Figure 18C:
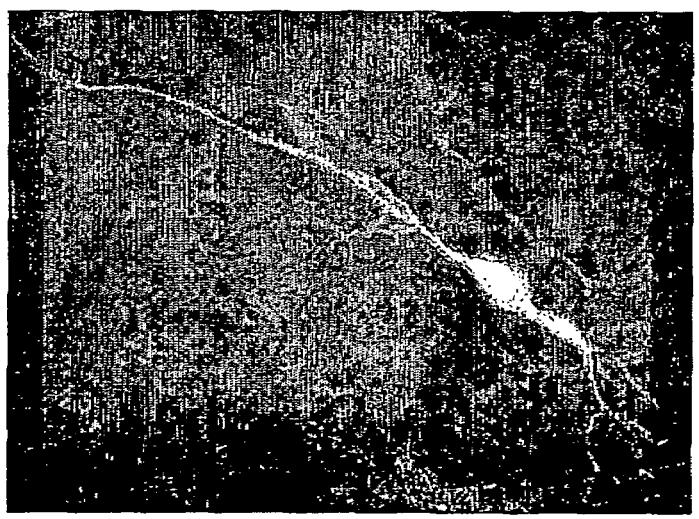
FIG. 18C illustrates the pattern of illumination with decreased excitation to the bright cell body used in experiment illustrated in FIG. 18B.

FIG. 18C illustrates the pattern of illumination with cell body masking that allowed the neuron to tolerate greater light exposure using an embodiment of the instant invention.

The spatial light modulator 60 shown in FIG. 3 may comprise a liquid crystal device (LCD), a digital nano- or micromirror device (DMD) and/or a nano- or micro-electro device. In an enabling embodiment and for transmissive displays, an LCD panel is placed between two polarizers. The incoming polarizer presents the LCD panel with a uniform, linearly polarized cone of light. Each pixel in the LCD panel can independently rotate the input polarized light to an angle dictated by the voltage addressed to that pixel. The outgoing polarizer then absorbs the rotated light to an extent dictated by the degree of rotation to create an image of differing intensities.

The inventor has found that while either a wire grid or polymer polarizer may be employed, desired qualities in choice of polarizer include heat tolerance, high extinction for cross polarized light, and high transmission for parallel polarized light. A specific polarizer envisioned for the invention's application is a heat tolerant and high contrast polymer polarizer (for example, certain polarizers made by Polatechno, Inc., in Japan; another source of high-quality polarizers includes the company Moxtek, Inc.).

It is known that LCD contrast can decrease with increasing temperature. The "clearing temperature" (the temperature at which an LCD panel looses contrast) for most LCDs is approximately 85 degrees C. While prototypes of the instant invention did not encounter the specific problem of the LCD reaching a temperature at or above 85 degrees C., the inventor remained ready to address this potentiality with known cooling methods, for example, a cooling fan to provide a remote fan-driven air stream.

Additional steps used to optimize LCD contrast include minimizing reflection off the exit polarizer. For instance, any wire grid polarizer which is high reflective should only be used as the input polarizer and not as an exit polarizer. An additional LCD compensation polarizer may be placed on the exit side of the LCD panel to improve image contrast.

Advantages of using an LCD in the present invention include the fact that LCD panels are relatively thin, and the further fact that the common x-y physical dimensions of LCD panels typically match the allowable dimensions of common field diaphragms used in typical fluorescence microscopes. Consequently, the LCD assembly of the instant invention can be positioned simply and directly within the field diaphragm slot in the epi-illumination unit of the typical fluorescence microscope, without needing to alter the optics of the typical microscope. Furthermore, LCD panels are relatively inexpensive.

Figure 16:
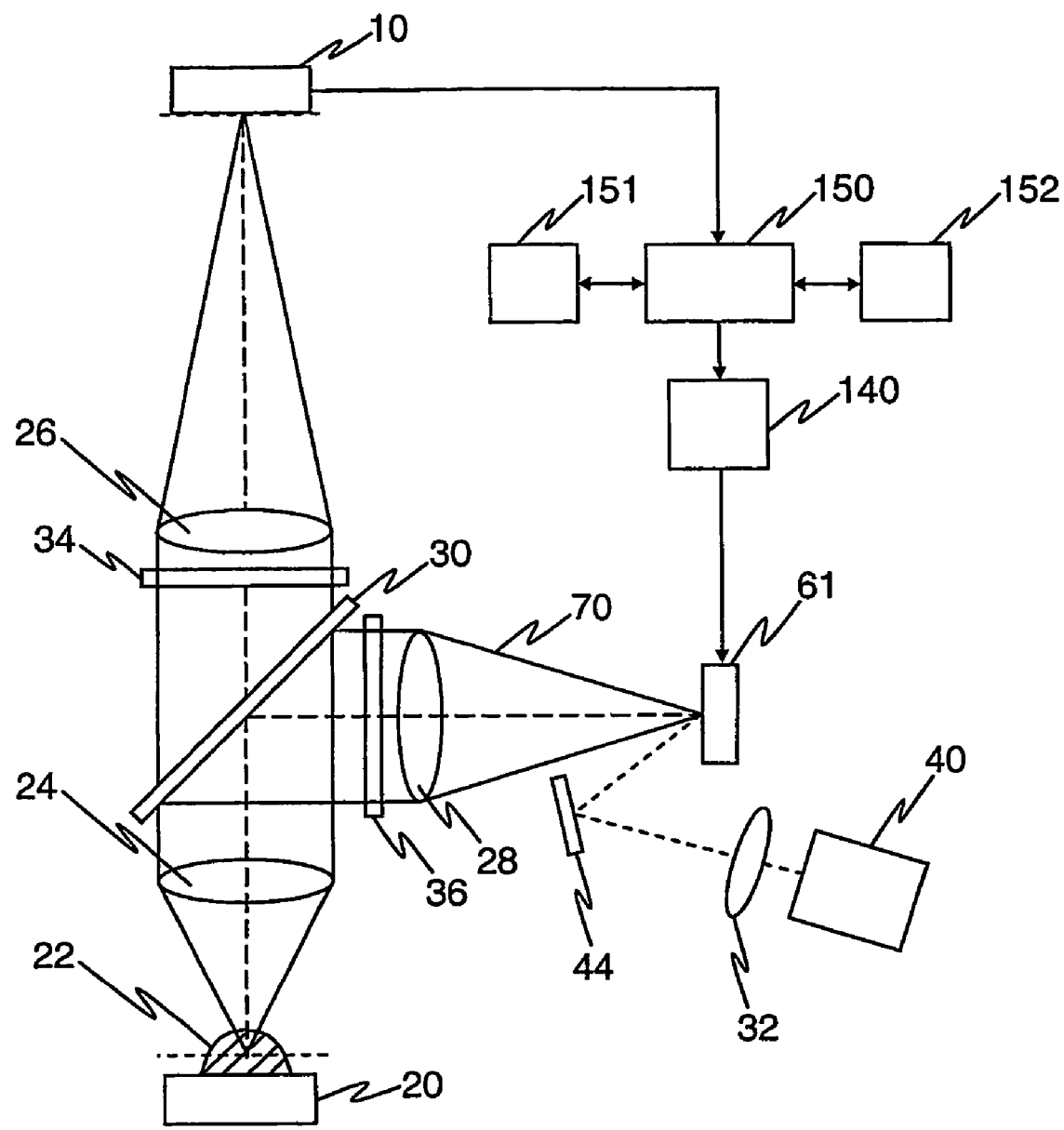
FIG. 16 illustrates an embodiment of the invention including the use of a Digital Micro-Mirror Device (DMD)

A digital micro-mirror device (DMD) may also be used as the high resolution spatial light modulator 60 as shown in FIG. 16. DMDs are also referred to as DLPs (digital light processors) by the main manufacturer of these devices (Texas Instruments). While the current trend is to label the noted digital micro-mirror devices as being "digital" and "micro," the ordinarily skilled artisan readily comprehends that such devices could also be analog, and/or smaller than micro (such as nano-sized) or even larger than micro-sized.

Current DMD technology differs from LCD technology by producing an 'all-or-none' signal for each pixel. By way of explanation, DMD technology micro-mirrors are connected to pivots fabricated as a large, closely packed array. Each micro-mirror can be independently addressed and controlled so as to be oriented in one of two directions (if not more than two directions). In an "on" position, light is reflected into the microscope's imaging path, and in the 'off' position light is directed away from the microscope's imaging path.

Figure 5A:
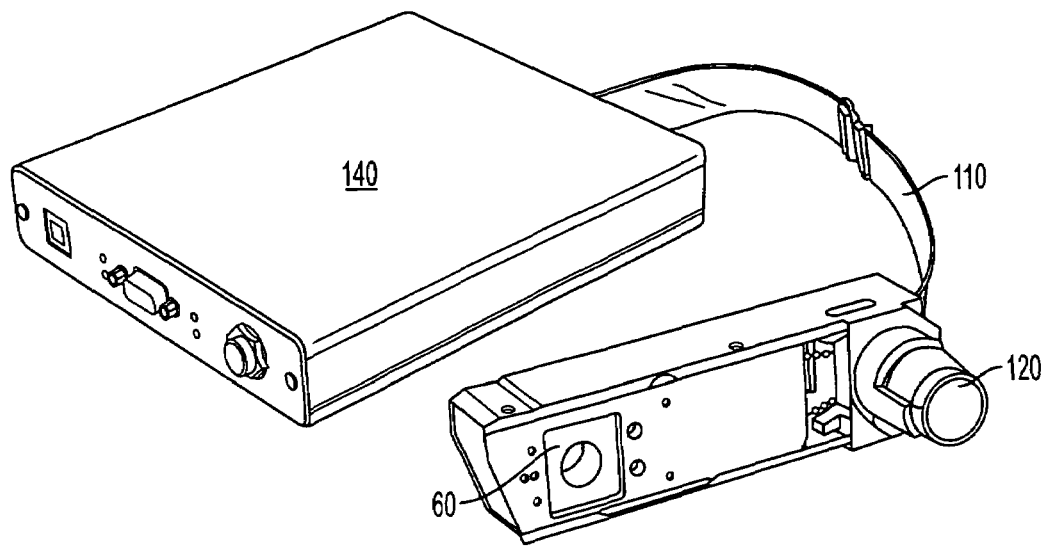
FIG. 5A is an illustration of the present invention including an LCD mounted on a slider and connected to an LCD drive controller by a ribbon cable.
Figure 5B:
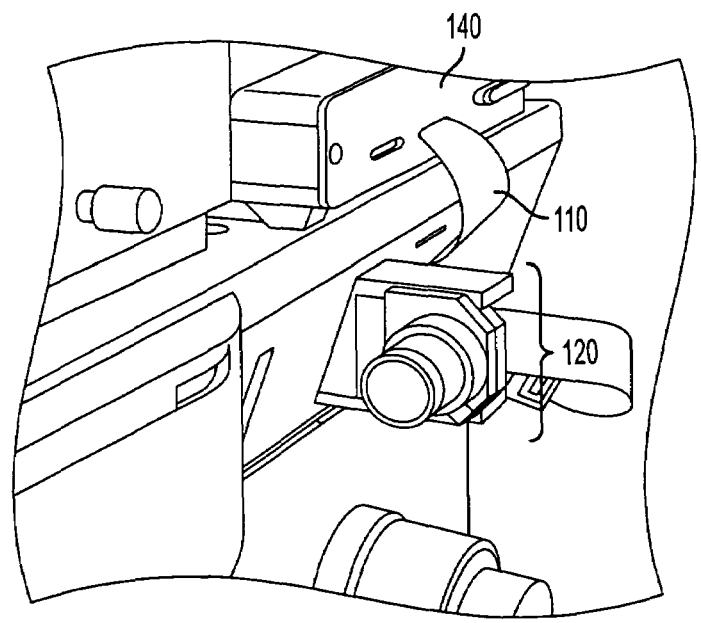
FIG. 5B is an illustration of the present invention including the slider of FIG. 5A mounted in the field diaphragm slot of the epifluorescence unit of a Nikon microscope.

An exemplary embodiment of the present invention comprising the slider 120 containing the LCD panel and the LCD controller is shown in FIG. 5A. The LCD is connected to the slider by a ribbon cable 110. As shown in FIG. 5B, the LCD 60 (mounted in the slider 120) is capable of being snugly positioned in the field diaphragm slot 130 of a common microscope (e.g., the inventor utilized a Nikon upright microscope's epi-fluorescence unit). Other LCD panels could be used in similar fashion with other common microscopes, such as Olympus microscopes, Leica microscopes, or Zeiss microscopes. The spatial light modulator may be placed in the epi-illumination paths of either upright of inverted microscopes.

Figure 6:
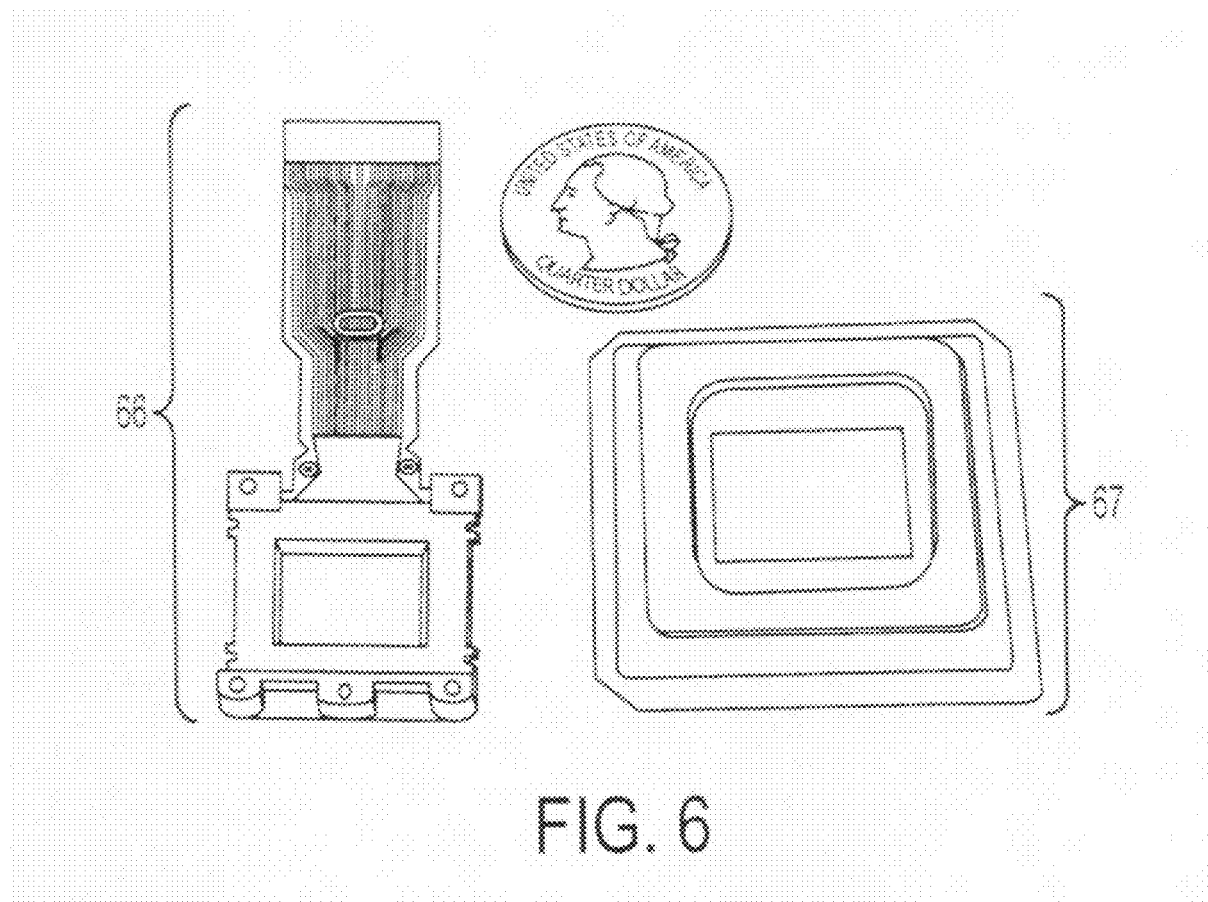
FIG. 6 is an image of components of an embodiment of the present invention including a liquid crystal display and a digital micro-mirror device.

FIG. 6 illustrates a representative LCD panel 66 that can be used as the active element in a LCD based spatial light modulator 60. Towards the right side of FIG. 6 is a representative DMD 67 that could be used for in a DMD based spatial light modulator.

Figure 7:
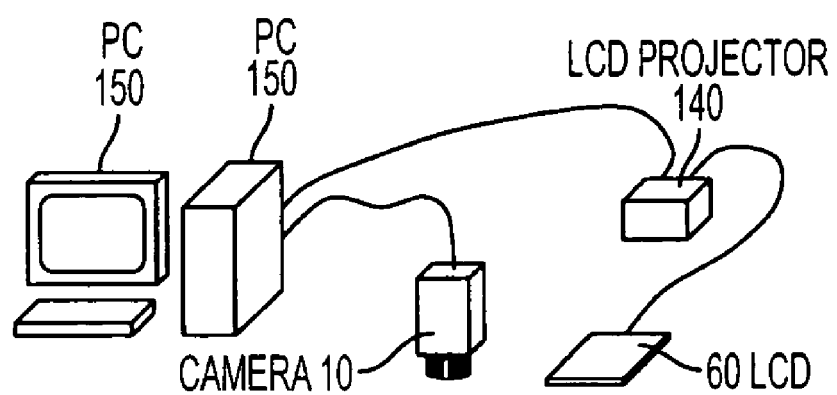
FIG. 7 illustrates an schematic of the invention including mechanical and electrical components separate from a microscope.

FIG. 7 illustrates mechanical and electrical hardware for implementation of an embodiment of the invention (for ease of understanding, like components are labeled identically to prior figures). As shown in FIG. 7, a CCD 10 interfaces with a computer 150 via a frame grabber card within the PC. Image processing software within the computer 150, with or without user input, analyzes a CCD image and computes a corrective modulation for the spatial light modulator 60 to thereby discriminately excite the sample being viewed. The CCD 10 takes its image from a sample being viewed by a microscope, for instance (the microscope is not shown).

The computer 150 may determine if the image taken is over or under exposed. Alternatively, a user may enter values to drive the excitation light modulator 60 to produce a discriminating excitation illumination light based on knowledge of the sample currently under observation. A previously stored set of values may also be retrieved and supplied as control signals to the modulator.

The camera 10, frame grabber and computer 150 may be off-the-shelf items. The computer 150 includes a graphical user interface (GUI) and a plug-and-play "driver" for connecting to the LCD controller 140. The LCD controller 140 drives the LCD panel serving as the spatial light modulator 60.

Figure 8:
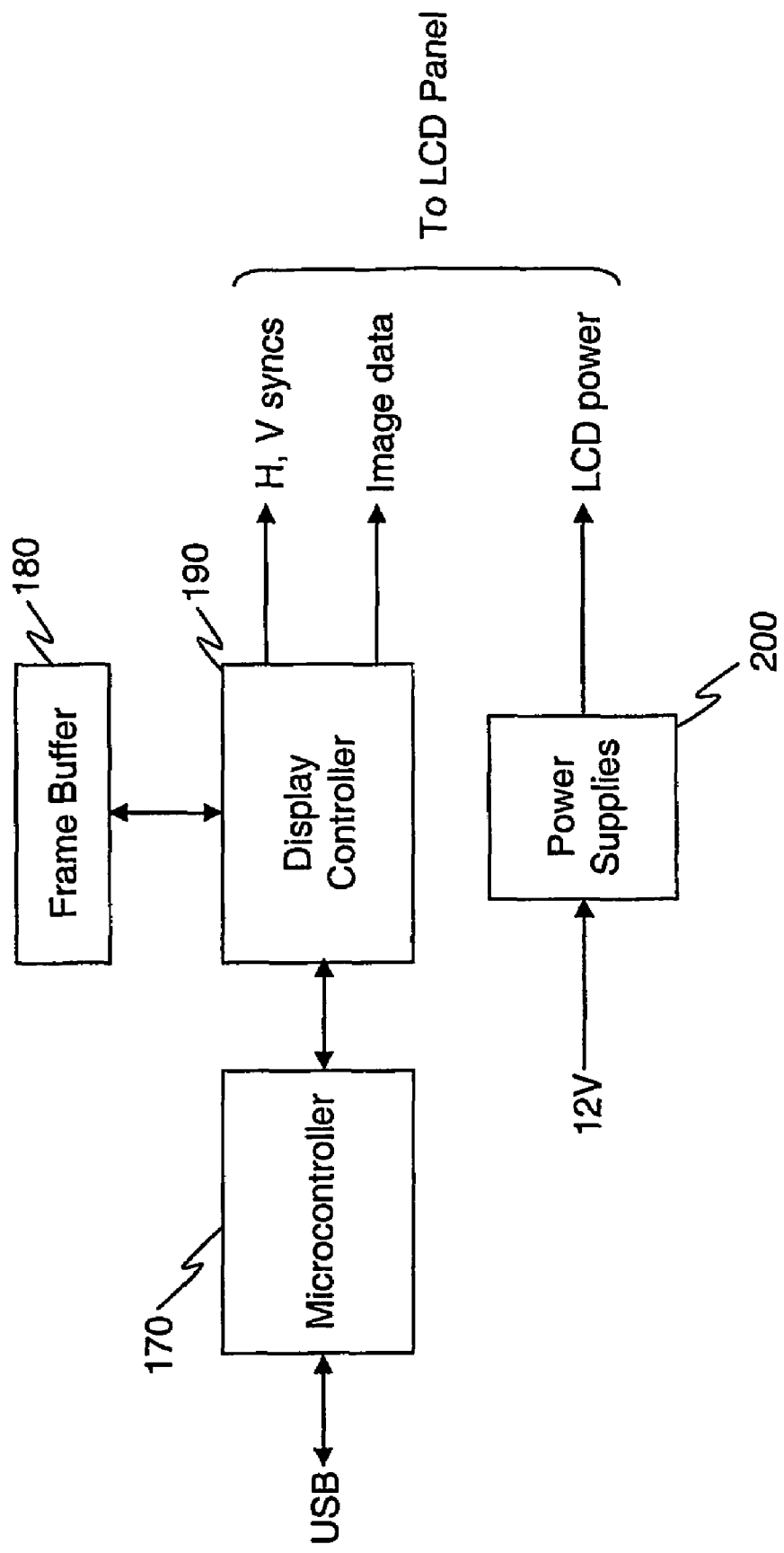
FIG. 8 illustrates an embodiment of the invention including the sub-components of an LCD projector/controller.

FIG. 8 illustrates exemplary sub-components of the Liquid Crystal Device controller 140. The controller 140 may connect to the computer 150 via a Universal Serial Bus (USB) interface. A microcontroller 170 provides the controller's USB connection. The corrective image is received by the microcontroller 170 from the computer 150.

The computer receives the original image from the CCD 10 potentially using any one of many commercially available image acquisition software and computer interface. One example of commercial image acquisition software is IPLab™ from Scanalytics. The computer may utilize additional software (described below) to interface with the LCD controller. The computer, image acquisition software, and/or user perform a qualitative and quantitative analysis of the original image to determine the most-likely modulation scheme for driving the spatial light modulator 60 to produce a qualitatively pleasing image (additionally and/or alternatively, a user may enter modulation characteristics desired for a particular sample). The modulation scheme produced by the computer 150 may be stored in a frame buffer 180 of the controller/projector 140. The frame buffer 180 is coupled to a display controller 190. The display controller 190 generates horizontal and vertical synchronization signals for the LCD panel 60 and transmits the contents of the frame buffer 180 to the panel 60.

Software useful for implementing the present invention includes a graphical user interface (GUI) which provides manual functionality of alignment and image processing.

The alignment of the LCD image mask in the illumination path is critical for the precise masking of structures in any microscope image plane. The goal is to achieve a precise co-registration of LCD pixels with the corresponding pixels of the electronic image sensor. At least three parameters require adjustments. First, the location of the center of the spatial light modulator projected on the target specimen must also correspond to the center location of the image detector. Second, the size of the pattern projected onto the target specimen must correspond to the size of the pattern detected by the image sensor. Thirdly, the orientation of the projected pattern must correspond to the orientation of the pattern detected by the image sensor. A fourth parameter, optical distortions, may require adjustment if significant optical distortion exists between the image forming and specimen illumination optical paths. Significant optical distortions are not usually observed in the center of the field of view for high quality scientific microscopes.

The alignment and co-registration of the image detector and spatial light modulator pixels may utilize mechanical positioning of the spatial light modulator and/or image detector. However, the preferred method for routine alignment and co-registration is to electronically control the output of the spatial light modulator either in a manual process or an automated algorithm. In the manual alignment process a target pattern is sent to both the spatial light modulator and the image acquisition software. The pattern is projected as an overlay over the image acquired by the electronic image sensor. The pattern send to the spatial light modulator is projected onto a smooth flat target. In this manner the image acquisition software can display both the expected pattern and the pattern actually projected onto the target. The user can then manually adjust the x,y position of the pattern, the magnification, and rotational orientation of the spatial light modulator via the LCD/DMD controller. Once adjusted the settings can be saved by the software/computer for subsequent use until there is a change to the optics or the slider position. An example of a target pattern may consist of a crosshair located at the center and brackets located just within the four corners of the electronic image sensor. If correction of optical distortion is required, the target pattern will contain grid patterns that can best detect the optical distortion. A morphing algorithm will be used to correct the optical distortion.

Figure 9A:
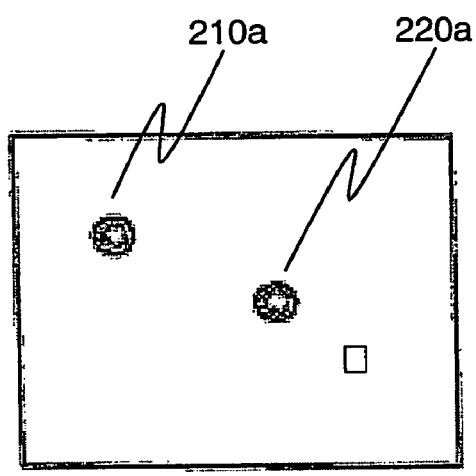
FIG. 9A illustrates an image projected by the LCD of the present invention including a calibration technique where two points are projected by the LCD projection array.
Figure 9B:
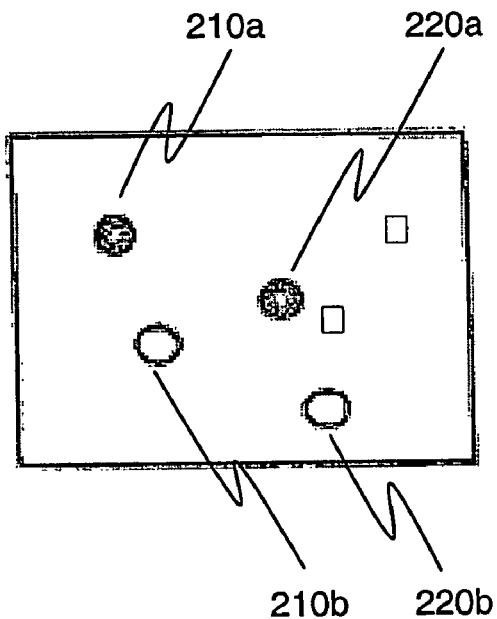
FIG. 9B illustrates a co-registration of the two points shown in FIG. 9A with a CCD collection array.

FIGS. 9A and 9B illustrate an example of an automated algorithm for optimal alignment and co-registration of the LCD image to the CCD. Dots 210a and 220a illustrate the two reference points needed to provide a two-dimensional alignment. The two points 210a and 220a are projected by the LCD excitation light modulator 60 and captured by the CCD 10, as shown in FIG. 9A. The location of the two circles is predetermined on the CCD camera to provide an x-y coordinate "target."

FIG. 9B is an overlay of the LCD projected image captured by the CCD and the expected target locations of the LCD projected image on the CCD, showing how dots 210a and 220a do not quite line up with dots 210b and 220b (presumably this is because an objective has been changed, or because the slide sample was adjusted or for any reason resulting in the image not being viewed in an original state). An automated algorithm is capable of calculating the necessary translation, rotation, and magnification of the calibration points to be used to generate LCD masks with a co-registration of the LCD mask and the CCD such that dots 210a and 220a align with dots 210b and 220b, respectively.

A task often utilized in fluorescence microscopy is the process of masking the illumination/excitation area in a field of view. This functionality is of interest for several reasons. First, when a very bright structure in an image field dominates the dynamic range of the CCD camera, darker and smaller structures of interest become barely visible and thus difficult or impossible to analyze. In this situation, an investigator often limits the area of excitation in the field of view to exclude the bright structure.

Second, within a field of view it may be of interest to continuously image a structure while minimizing excitation of nearby structures. This situation often arises when an investigator is performing live cell imaging on one cell or part of one cell in a field of other live calls and wants to minimize the exposure of the other cells and parts of the same cell. FIGS. 18A-C illustrate the effects of phototoxicity during live cell fluorescence imaging.

Both problems are often addressed with commercially available field iris insets, which limit the excitation field to a defined field of view. These mechanical barriers are of a single shape (usually a circle or a square) and size, and are in a fixed position in the excitation path, making their use limited and inflexible. Furthermore, it is often desirable not to block illumination completely to the neighboring structures. Even existing electronically addressable field stops can not provide precise graded illumination.

FIGS. 10A-D illustrate an embodiment of the present invention including an interface that allows a user to custom-design a Field Iris Mask (FIM). FIGS. 10A-D are theoretical set of masks created with either a transparent (shown by FIGS. 10B and 10D as representing no density) or blocking (100% density, as shown by FIGS. 10A and 10C) background pallet, in which a rectangle, or a circle or free-form shape is defined. Areas of interest (AOI) are user-defined through a portion of a GUI software implemented in a computer 150 (such as the computer 150 shown in FIG. 7). A user chooses from AOI tools, which contain pre-set shapes (e.g., a circle, a square, a rectangle and/or an ellipse) or a freeform tool which is interactively created via mouse interaction.

Because of differences in samples and in the desired structures that the user may wish to bring out, the instant invention provides CCD/LCD contrast transfer functions or density transfer functions that can be used to provide graded level of feedback illumination. These functions may include linear, logarithmic, threshold, or user-defined density transfer functions.

Examples of logarithmic functions are illustrated in FIGS. 11A-C. In these examples, an image was collected on a 12 bit CCD camera (4096 level resolution) with a maximum image intensity of 20,000 units. FIGS. 11A and 11B illustrate the detected intensity of the CCD camera (y-axis) versus the optical intensity of the image(x-axis). The detected intensities are shown as solid lines. The unmasked theoretical object intensity is shown as a dotted line in FIG. 11A. FIG. 11B shows a logarithmic density transfer function which provides either of an automated or semi-automated control of the excitation light modulation. Most cellular structures saturated at a value of 4096 as shown by the horizontal solid line in the top panel of FIG. 11A and as white on the gradient scale in the center panel of FIG. 11A.

A logarithmic density transfer function is shown in the column of FIG. 11B. The top panel of FIG. 11B shows the final correlation between the un-masked object intensity and the masked intensity that falls within the dynamic range of the CCD camera. The gray scale is shown in the center panel. The transmittance of the mask for this object using the logarithmic density transfer function is shown in the bottom panel of FIG. 11B. As stated previously, in various embodiments of the instant invention, the computer 150 and the controller 140 (such as those shown in FIG. 3) are capable of implementing the logarithmic functions shown in FIGS. 11A-C in either of an automatic or semi-automatic fashion based on the fluorescent emissions detected by the imaging device 10.

FIGS. 17B illustrate the benefits of the current invention on image quality as compared to the conventional system depicted by FIG. 17A. Specifically, the distortion in size created by pixel saturation at the bright cell body is eliminated in FIG. 17B as compared to FIG. 17A. Further, the distortion in the relative brightness of structures of near by to distant structures is eliminated in FIG. 17B as compared to FIG. 17A.

Additionally, the signal-to-noise ratio of dim structures is also improved in FIG. 17B as compared to FIG. 17A.

FIGS. 18A-C illustrate the ability of the present invention to decrease the rate of photo-toxicity in live cell imaging. FIG. 18A illustrates an unmasked live cell with associated photo-toxicity due to a bright cell body. FIGS. 18B and 18C illustrates a partial masking of the bright cell body containing large amount of fluorescent dyes, thereby increasing the allowable illumination time by greater than four-fold before appearance of pathological changes on axonal and dendritic processes.

Another common problem in fluorescent microscopy is an out-of-focus blur causing poor image quality. Confocal microscopy heretofore has not been easily implemented. There may be situations where an image could be greatly improved if only bright out-of-focus blur could be eliminated from a specific plane. Because of the confocal nature of the instant invention's spatial light modulator controlled excitation illumination system, it is possible to attenuate out-of-focus blur that occurs in a conventional wide-field microscope as described below.

Figure 12A:
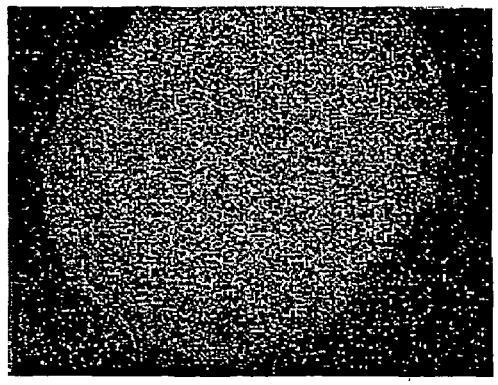
FIG. 12A illustrates a conventional method of viewing a sample with more than one plane of focus, causing an out-of-focus image.
Figure 12B:
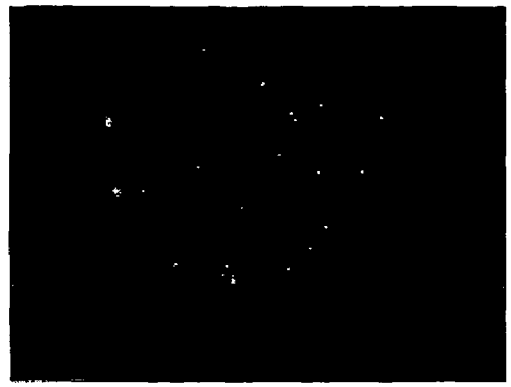
FIG. 12B illustrates an embodiment of the invention with the ability to mask an out-of-focus structure without obscuring the in-focus structure using confocal masking.

FIGS. 12A and 12B illustrate the invention's technique of masking an out-of-focus signal. FIG. 12A illustrates a field diaphragm plane that is conjugate to the image plane. Patterns projected from the spatial excitation light modulator 60 positioned at the field diaphragm plane are confocally projected (masked) onto the sample being observed. If the axial position of the spatial excitation light modulator 60 is shifted, the masking action also shifts by a distance proportional to the ratio of the focal length of the objective and tube lens. This principle is shown by FIGS. 12A and 12B, wherein a pair of small fluorescent spheres was placed in one plane and a pair of larger spheres was placed in another plane.

FIG. 12A illustrates the expected image when the focus is on the small spheres. Note that the out-of-focus spheres make the image in FIG. 12A practically impossible to read. In contrast, the instant invention, by first taking an in-focus image of the fluorescent emittance of the two larger spheres, inverting the excitation illumination at the modulator 60 as compared to the detected fluorescent emittance and shifting the modulator 60 by an appropriate distance, provides the advantageous result of selective masking the two out-of-focus spheres without changing the image of the in-focus spheres (as shown in FIG. 12B). The result is a qualitatively and quantitatively pleasing image.

Figure 15:
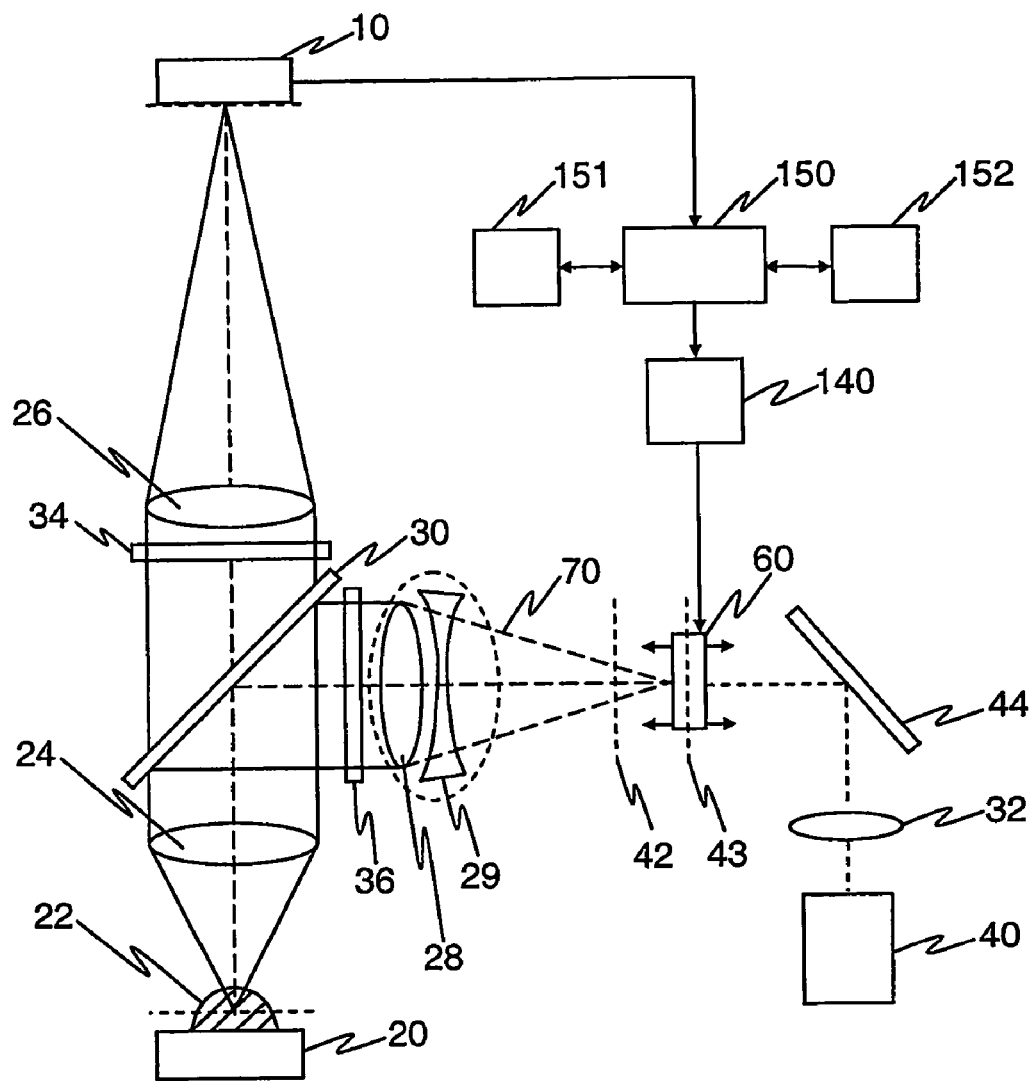
FIG. 15 illustrates an embodiment of the invention including the capability to change the focal length of the illumination tube lens thereby allowing changes in the relative magnification of the pattern displayed by the spatial light modulator and that detected by the image sensor.

The concepts related in FIGS. 12A and 12B are also shown in FIG. 15. Similar features previously discussed in relation to FIGS. 3 and 12A and 12B are not re-discussed so as to avoid redundancy.

In FIG. 15, the spatial light modulator 60 is capable of movement along the illumination axis. The modulator 60 may be moved by any of sliding wedges, piezo electric actuators, a stepper motor actuator, and/or other mechanical/electrical/pneumatic systems. The preferred method is through the coupled rotation of multiple threaded posts on which the spatial light modulator is mounted. The dotted line shown by numeral 42 represents the previous field diaphragm plane prior to movement of the modulator 60 to a different plane shown by the dotted line at numeral 43. Movement of the modulator 60 allows for confocal image masking such as that described in relation to FIGS. 12A and 12B. Furthermore, in very thin specimens the thin dark grid pattern inherent to LCDs will appear in the acquired image. Therefore, it may be advantageous to move the position of the spatial light modulator slightly away from the conjugate image plane in order to defocus the fine grid patterns of the LCD.

In most modern fluorescent microscopes the lens for image formation 26 is designed to be different from the lens 28 for specimen illumination. The previous can result in markedly different magnification of patterns located at image plane 42 and the conjugate image plane at the detector 10. Therefore, a single LCD pixel typically corresponds to 16 or 25 CCD pixels, which is not an optimal utilization of LCD resolution. The solution is to increase the focal length of the epi-illumination tube lens 28. The change in focal length of the epi-illumination lens is represented by the dotted circle enclosing lens 28 and 29. The increase in the focal length of this tube lens is particularly important for large size spatial light modulators. With any significant change in the tube lens the spatial light modulator will also need to be repositioned to a plane close to its new conjugate image plane 43.

FIG. 15 also shows an alternative arrangement of the light source 40 being reflected by mirror 44 to the light modulator (an LCD in FIG. 15) through condenser 32.

FIG. 16 illustrates a microscope system similar in nature to that shown in FIG. 15, but includes a DMD instead of an LCD for the modulator 60. Similar features previously discussed in relation to FIGS. 3 and 15 are not re-discussed so as to avoid redundancy. In contrast to LCD of the transmissive type, a DMD spatial light modulator 60 creates image patterns by deflecting light at each pixel. In response to an ON input voltage, the mirror deflects the incident light into the clear aperture of the illumination tube lens 28. The path of the light deflected in the ON state is represented by the dotted line in FIG. 16. In response to an OFF input voltage, the mirror deflects the incident light outside of the clear aperture of the lens 28 (outside of cone 70).

The ability to modulate the DMD 60 to achieve a grayscale pattern is different than that of an LCD. Whereas the LCD achieve gray levels by graded rotation of the incident polarized light, a DMD achieves gray levels by "flickering" between the ON and OFF modes of the individual micromirrors. An example (incorporated herein by reference) of grayscale levels using DMD technology is described by Larry J. Hornbeck in *Digital Light Processing for High-Brightness, High-Resolution Applications* (available at www.vxm.com/TIDLP.html). In this white paper, Hornbeck describes achieving grayscale brightness levels by modulating the binary pulse width of the incident light. By rapidly moving the micro mirrors from an "on" position to an "off" position multiple times in an integration period of the electronic detector 10, a certain level of grayscale fluorescence can be realized.

For example, using a Texas Instruments micro mirror device, a user can expect a switching time from "on" to "off" of about 15 microseconds. The typical integration time for a CCD to capture a fluorescent image is approximately between 1 ms to 1000 ms. A grayscale is determined by the percentage of time that the micro mirror is in the "on" state versus the "off" state during the integration period.

A typical DMD accepts electrical words which are used to represent grayscales. These words are encoded in binary form. For example, a 10-bit word may define 1024 gray levels. A 4-bit word will have a time duration with relative values of 1, 2, 4 and 8 within the integration time window.

Figure 13A:
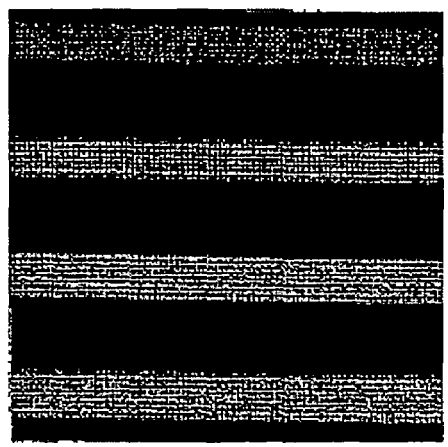
FIG. 13A illustrates an embodiment of the invention including a reference image of a set of white bars against a black background that is useful for calibrating contrast, resolution and aberration.
Figure 13B:
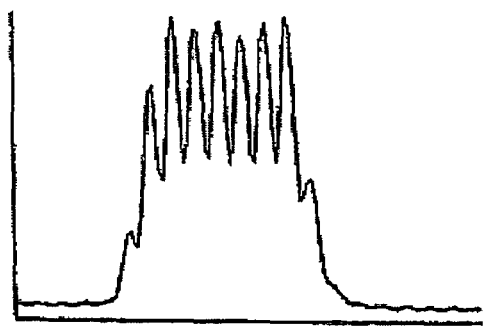
FIG. 13B illustrates an embodiment of the invention where one white bar from FIG. 13A has been scanned to thereby allow a measure of absolute intensity, resolution and aberration (as detected by each CCD pixel)

A further embodiment of the present invention provides the ability to calibrate for contrast, resolution and aberration, as shown in FIGS. 13A and 13B. In FIG. 13A, a command image is taken of a set of white bars of differing brightness as against a black background. These bars are then projected onto a flat surface, such as a front surface mirror. The grid pattern on the white bars represents the fine grid that separates individual LCD pixels. The ability to detect these grids provides a measure of spatial resolution. The straightness of the grids provides a measure of potential aberration. Further, as shown in FIG. 13B, a vertical line scan across just one strip is used to measure the absolute intensity detected by each CCD pixel, including resolution and contrast.

FIGS. 14A and B are schematic representations of exemplary, non-limiting embodiments of how a modulator may be moved to change the magnification of the modulated excitation light. Skilled artisans readily comprehend that a modulator may be re-positioned using other mechanical, electrical, and/or additional repositioning means.

FIG. 14A is a top-view and FIG. 14B is a side view of a Liquid Crystal Device 60 attached to a sliding fork 230. By adjusting the sliding fork 230 in the directions of arrows 240, the LCD moves to adjust to differing physical dimensional placement, thereby adjusting the focus of any projected image.

The above-identified invention may be embodied in a computer program product, as will now be explained.

On a practical level, the software that enables a computer system to perform the operations described above may be supplied on any one of a variety of media. Furthermore, the actual implementation of the approach and operations of the invention are actually statements written in a programming language. Such programming language statements, when executed by a computer, cause a computer to act in accordance with the particular content of the statements. Furthermore, software that enables a computer system to act in accordance with the invention may be provided in any number of forms including, but not limited to, original source code, assembly code, object code, machine language, compressed or encrypted versions of the foregoing, and any and all equivalents.

One of skill in the art will appreciate that "media", or "computer-readable media", as used here, may include a diskette, a tape, a compact disc, an integrated circuit, a ROM, a CD, a cartridge, a memory stick, a card, a remote transmission via a communications circuit, or any other similar medium useable by computers known now or developed hereafter. For example, to supply software for enabling a computer system to operate in accordance with the invention, the supplier might provide a diskette or might transmit the software in some form via satellite transmission, via a direct telephone link, or via the Internet. Thus, the term, "computer readable medium" is intended to include the entire foregoing and any other medium by which software may be provided to a computer.

Although the enabling software might be "written on" a diskette, "stored in" an integrated circuit, or "carried over" a communications circuit, it will be appreciated that, for the purposes of this application, the software will be referred to as being "on" the computer readable medium. Thus, the term "on" is intended to encompass the above and all equivalent ways in which software is or can be associated with a computer readable medium.

For the sake of simplicity, therefore, the term "program product" is thus used to refer to a computer readable medium, as defined above, which bears, in any form, software to enable a computer system to operate according to the above-identified invention. Thus, the invention is also embodied in a program product bearing software which enables a computer to perform according to the invention.

The invention is also embodied in a user interface invocable by an application program. A user interface may be understood to mean any hardware, software, or combination of hardware and software that allows a user to interact with a computer system. For the purposes of this discussion, a user interface will be understood to include one or more user interface objects. User interface objects may include display regions, user activatable regions, and the like.

As is well understood, a display region is a region of a user interface which displays information to the user. A user activatable region is a region of a user interface, such as a button or a menu, which allows the user to take some action with respect to the user interface.

A user interface may be invoked by an application program. When an application program invokes a user interface, it is typically for the purpose of interacting with a user. It is not necessary, however, for the purposes of this invention that an actual user ever interact with the user interface. It is also not necessary, for the purposes of this invention, that the interaction with the user interface be performed by an actual user. That is to say, it is foreseen that the user interface may have interaction with another program, such as a program created using macro programming language statements that simulate the actions of a user with respect to the user interface.

The previous description of embodiments is provided to enable a person skilled in the art to make and use the present invention. Various modifications to these embodiments will be readily apparent to those skilled in the art, and the generic principles and specific examples defined herein may be applied to other embodiments without the use of inventive faculty. For example, some or all of the features of the different embodiments discussed above may be deleted from the embodiment. Therefore, the present invention is not intended to be limited to the embodiments described herein but is to be accorded the widest scope defined only by the claims below and equivalents thereof.

What is claimed is:

1. A method for discriminately exciting a fluorescent sample comprising:
    detecting an image;
    feeding light information derived from the detected image to a spatial light modulator; and
    modulating spatial light based at least in part on said light information; wherein
    said image is detected from emitted light released from a fluorescent sample being excited by said modulated spatial light; and
    said modulated spatial light is discriminately emitted by said spatial light modulator to the fluorescent sample based at least in part on said light information; and further wherein
    said light information comprises data including brightness levels and spatial distribution of the level of light emitted by the fluorescent sample, wherein said spatial light modulator moves along the optical axis of illumination.

2. The method of claim 1, further comprising:
    recording said light information to a memory; wherein
    after said light information is recorded within said memory, said recorded light information allows a user to recall and recurrently implement a discriminate excitation light to the fluorescent sample from said spatial light modulator.

3. The method of claim 1, wherein an intensity of said excitation light for exciting the fluorescent sample is substantially inversely proportional to an intensity of said light emitted by the fluorescent sample.

4. The method of claim 1, further comprising:
    recording said light information to a memory; wherein
    after said light information is recorded within said memory, said recorded light information allows a user to recall and recurrently implement a discriminate excitation light to the fluorescent sample from said spatial light modulator; and varying said excitation light for exciting the fluorescent sample on a point-by-point basis based on intensities of said light emitted by the fluorescent sample; where
said excitation light is substantially inversely proportional to an intensity of said light emitted by the fluorescent sample.

5. A microscope comprising:
an image detector;
a spatial light modulator, wherein said spatial light modulator is coupled to said image detector, said image detector is capable of detecting light emitted from a flourescent sample being excited by an excitation light modulated by said spatial light modulator, said spatial light modulator discriminately emits said excitation light to the flourescent sample based on information provided from at least said image detector, and said information comprises data including brightness levels and the spatial distribution of the light emitted by the flourescent sample; and
at least one objective, wherein said spatial light modulator moves along the optical axis of illumination.

6. The microscope of claim 5, wherein said image detector is at least one of a charged coupled device, a CMOS camera, a video camera, and a photodiode array.

7. The microscope of claim 5, wherein said spatial light modulator comprises is selected from the group consisting of a liquid crystal display, a micro-mirror device, an array of light-emitting diodes and a fiber bundle, an array of light bulbs, and an electro-mechanical device.

8. The microscope of claim 5, further comprising:
a memory, wherein
said memory is coupled with said image detector; and
said information is recorded within said memory, said recorded information allowing a user to recall and recurrently implement a discriminate excitation light to the fluorescent sample from said spatial light modulator.

9. The microscope of claim 5, wherein an intensity of said excitation light for exciting the fluorescent sample is substantially inversely proportional to an intensity of said light emitted by the fluorescent sample.

10. The microscope of claim 5, wherein an intensity of said excitation light for exciting the fluorescent sample varies on a point-by-point basis with intensities of said light emitted by the fluorescent sample.

11. The microscope of claim 5, further comprising a computer for controlling said spatial light modulator through manipulation of said information.

12. The microscope of claim 5, further comprising:
a memory; wherein
said excitation light for exciting the fluorescent sample varies on a point-by-point basis based on said light emitted by the fluorescent sample; and
said excitation light is substantially inversely proportional to an intensity of said light emitted by the fluorescent sample; where
said information is recorded within said memory, said recorded information allowing a user to recall and recurrently implement a discriminate excitation light to the fluorescent sample from said spatial light modulator.

13. A computer program product for enabling a computer to discriminately excite a fluorescent sample comprising:
a computer readable medium, and software instructions, on the computer readable medium, for enabling the computer to perform predetermined operations comprising:
detecting an image;
feeding light information derived from the detected image to a spatial light modulator; and
modulating a spatial light with said spatial light modulator based at least in part on said light information; wherein
said image is detected from light released from a fluorescent sample being excited by said modulated spatial light; and
said modulated spatial light is discriminately transmitted by said spatial light modulator in at least a grayscale manner to the fluorescent sample based on said light information; and further wherein
said light information comprises information which distinguishes between variations in the level of light emitted by the fluorescent sample, wherein said spatial light modulator moves along the optical axis of illumination.

14. A computer program product for enabling a computer to discriminately excite a fluorescent sample according to claim 13, further wherein said predetermined operations comprise illuminating said fluorescent sample with epi-illumination.

15. The method of claim 1, further including:
emitting said spatial light in a predetermined illuminating light pattern on said sample.

16. The microscope of claim 5, wherein said spatial light modulator emits a predetermined illuminating light pattern on said sample.

17. The microscope of claim 5, wherein said spatial light modulator modulates based on feedback from said image detector and an operator input.

18. The microscope of claim 5, wherein said spatial light modulator modulates based on feedback from said image detector.

* * * * *